United States Patent [19]

Laffitte et al.

[11] Patent Number: 5,434,285
[45] Date of Patent: Jul. 18, 1995

[54] CHIRAL PHOSPHINITE-BORANES AND THEIR PREPARATION AND USE

[75] Inventors: Jean A. Laffitte, Pau; Sylvain Jugé, Orsay; Jean P. Genet, Verrières le Buisson; Massoud Stephan, Paris, all of France

[73] Assignee: Societe Nationale Elf Aquitaine, Courbevoie, France

[21] Appl. No.: 104,023

[22] PCT Filed: Feb. 13, 1992

[86] PCT No.: PCT/FR92/00143
§ 371 Date: Oct. 7, 1993
§ 102(e) Date: Oct. 7, 1993

[87] PCT Pub. No.: WO92/14538
PCT Pub. Date: Mar. 9, 1992

[30] Foreign Application Priority Data

Feb. 13, 1991 [FR] France .................................. 91 01674

[51] Int. Cl.$^6$ .............................................. C07F 7/02
[52] U.S. Cl. .................................................. 556/402
[58] Field of Search .................. 568/2; 556/402; 564/8

[56] References Cited

U.S. PATENT DOCUMENTS 5,264,602  11/1993  Juge et al. ............................ 556/402

FOREIGN PATENT DOCUMENTS 9100286  1/1991  WIPO .

OTHER PUBLICATIONS

S. Juge et al., "Efficient asymmetric synthesis of optically pure tertary mono and diphosphine Ligands", Tetrahedron Letters, vol. 31, No. 44, 1990, Oxford, Great Britain, pp. 6357–6360.

*Primary Examiner*—Johann Richter
*Assistant Examiner*—John Peabody
*Attorney, Agent, or Firm*—Evenson, McKeown, Edwards & Lenahan

[57] ABSTRACT

The present invention relates, by way of novel industrial products, to the phosphinite-borane compounds of the general formula

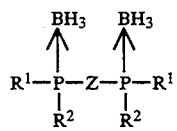 (X)

in which
$R^1$ and $R^2$, which are identical or different, are each a $C_1$–$C_{18}$-alkyl group, a $C_5$–$C_{18}$-cycloalkyl group, a $C_7$–$C_{18}$-aralkyl group or a $C_6$–$C_{14}$-aryl group, it being possible for each of these groups to carry functional groups, and F is a silicon containing bridging group.

These products are useful in the syntheses of chiral compounds.

2 Claims, No Drawings

CHIRAL PHOSPHINITE-BORANES AND THEIR PREPARATION AND USE

This application is a 371 of PCT/FR92/00143, filed Feb. 13, 1992.

1. Field of the Invention

The present invention relates to a novel class of phosphinite compounds, especially chiral phosphinite compounds. It relates more precisely to the phosphinite-borane compounds of formula $I_o$ below, in which the two phosphorus atoms are both complexed by (or bonded to) a borane group. These phosphinite-borane compounds carry one or more labile or substitutable groups permitting nucleophilic substitution, for example by an alkylating, cycloalkylating or arylating group.

The present invention further relates to the methods of preparing these phosphinite-borane compounds and to their uses in the preparation of diphosphines.

2. Prior Art

It is known that phosphinite compounds, and particularly those which are optically active, are industrially useful both per se and as starting materials for the preparation of other useful chiral products such as, in particular, phosphine oxides, phosphines, etc.

Numerous natural and synthetic products can now be prepared by asymmetric synthesis catalyzed by means of transition metals, and especially with catalysts containing optically active organophosphorus ligands. The asymmetric synthesis route makes it possible to obtain substances which are of value in the fields of agriculture, food, pharmacy or perfumery. Known examples illustrating said asymmetric synthesis route are the production of L-dopa, L-phenylalanine, menthol or citronellol.

The preparation of two compounds of the formula

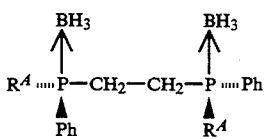
(I_A)

in which $R^A$ is ortho-anisyl or 2-naphthyl, is known from an article by the co-inventors of the present invention, namely S. JUGE et al., Tetrahedron Letters 31(no. 44) pages 6357–6360 (1990). The two compounds of formula $I_A$ according to scheme 2 in said article (see page 6358) are obtained from

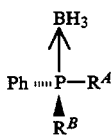
(I_B)

(in which $R^A$ is defined as indicated above and $R^B$ is $CH_3$) by the reaction of two mol of $I_B$ with (i) s-BuLi, then (ii) $CuCl_2$.

Said article, which is incorporated here by way of reference, also describes
(a) the preparation of the starting compounds of formula $I_B$, and
(b) the preparation of chiral 1,2-diphosphinoethane complexes of the formula

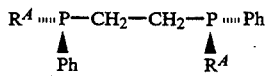

In another connection, two products of formula $I_o$, namely the compound in which $R^1$=Ph, $R^2$=Me $R^3$=Me and Z=$CH_2$ and, respectively, the compound in which $R^1$=Ph, $R^2$=Me, $R^3$=MeO and Z=$CH_2CH_2$, are known from Examples 21 and 22 of published PCT international patent application WO 91/00286 (publication date: 10th January 1991).

OBJECT OF THE INVENTION

One object of the invention is to provide novel phosphinite-borane compounds which are structurally different from those of the prior art cited above.

Another object of the invention is to provide a general method of preparing the novel compounds of formula $I_o$ below, and specific methods of preparing these compounds.

SUBJECT OF THE INVENTION

According to a first feature of the invention, a novel phosphinite compound substituted by $BH_3$ on the phosphorus is provided which is selected from the group consisting of the phosphinite-borane products of the general formula

(I_o)

in which
- $R^1$ and $R^2$, which are identical or different, are each a $C_1$-$C_{18}$-alkyl group, a $C_5$-$C_{18}$-cycloalkyl group, a $C_7$-$C_{18}$-aralkyl group or a $C_6$-$C_{14}$-aryl group, it being possible for each of these groups to carry functional groups,
- $R^3$ is a $C_1$-$C_{18}$-alkyl, $C_5$-$C_{18}$-cycloalkyl, $C_7$-$C_{18}$-aralkyl, $C_6$-$C_{14}$-aryl, $C_1$-$C_{18}$-alkoxy, $C_7$-$C_{18}$-cycloalkoxy, $C_7$-$C_{18}$-aralkoxy or $C_6$-$C_{14}$-aryloxy group, and
- Z is a bridge linking the two phosphorus atoms, said bridge being (i) a hydrocarbon chain having from 1 to 12 catenary C atoms, or (ii) a heterohydrocarbon chain containing from 1 to 12 catenary C atoms and at least one catenary heteroatom selected from O, S, Si, P and N,
- with the further condition that (i) Z is other than $CH_2$ when $R^1$=phenyl and $R^2$=$R^3$=methyl simultaneously, and (ii) Z is other than $CH_2CH_2$ when $R^1$=phenyl, $R^2$=methyl and $R^3$=methoxy simultaneously.

From a chiral point of view, a compound of formula $I_o$ can be represented by the following structure:

(I_o bis)

where $R^1$, $R^2$, $R^3$ and Z are defined as indicated above.

According to a second feature of the invention, a general method of preparing a phosphinite-borane compound of formula $I_o$ or $I_o$ bis is provided, said method comprising the reaction of an organometallic compound derived from a phosphinite-borane with a non-organometallic phosphinite-borane compound. Said organometallic compound is preferably an organolithium compound.

According to a third feature of the invention, the use of said phosphinite-borane compounds of formula $I_o$ or $I_o$ bis is provided for the preparation of other chiral compounds, especially the diphosphine-diborane products of formula X and the diphosphine products of formula IX:

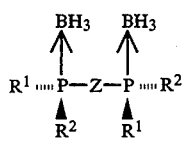 (X)

or

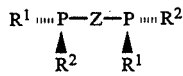 (IX)

where $R^1$, $R^2$ and Z are defined as indicated above.

More precisely, the phosphinite-borane compounds according to the invention are, in particular, converted to diphosphine-diborane compounds which are of high diastereoisomeric purity or essentially diastereoisomerically pure. These diphosphine-diborane compounds are then easily decomplexed (decomplexation is understood here as meaning the removal of the two borane groups, $BH_3$) at 50° C. by means of a secondary amine such as diethylamine.

ABBREVIATIONS

For the sake of convenience, the following abbreviations have been used in the present description:

bNp=beta-naphthyl (i.e. 2-naphthyl)
BNPE=bis(naphthylphenylphosphino)ethane, in particular the diastereoisomer (−)-BNPE of the formula

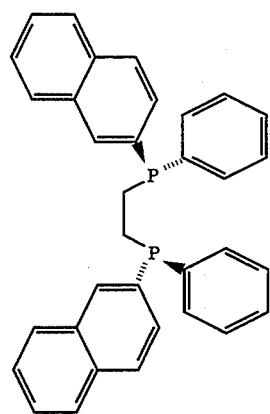

BNPPMDS=bis(2-naphthylphenylphosphinomethano)diphenylsilane, in particular the diastereoisomer of the formula

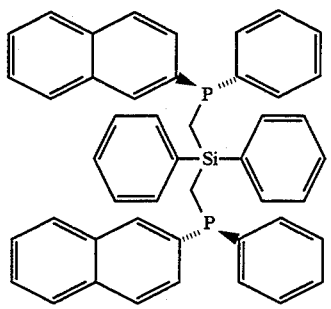

Bu=n-butyl
Bz=benzyl
DIPAMP=1,2-bis(phenyl-o-anisylphosphino)ethane, in particular the diastereoisomer (−)-DIPAMP of the formula

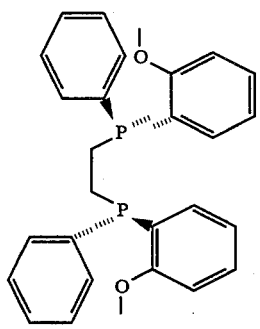

which is also called (R,R)-1,2-bis(phenylortho-anisylphosphino)ethane
Et=ethyl
i-Pr=isopropyl
Me=methyl
MeO=methoxy
M.p.=melting point
NMR=nuclear magnetic resonance
oAn=ortho-anisyl
Ph=phenyl
Pr=n-propyl
s-Bu=sec-butyl
t-Bu=tert-butyl
THF=tetrahydrofuran

DETAILED DESCRIPTION OF THE INVENTION $C_1$-$C_4$-Alkoxy, CN, $CF_3$, F, Cl, Br and I groups may be mentioned among the functional groups which are included in the definitions of $R^1$ and $R^2$ and which are suitable according to the invention. Thus $R^1$ and $R^2$ can contain one or more substituent groups selected from $C_1$-$C_4$-alkoxy, CN, $CF_3$, F, Cl, Br, I and mixtures thereof. Preferably, "functional" groups will be substituted on the aryl fragment of the aryl and aralkyl groups of $R^1$ and $R^2$.

The hydrocarbon chain of the bridge Z is either an unsaturated hydrocarbon chain or a saturated hydrocarbon chain.

Said bridge Z will preferably have one of the following structures:
(a) —$(CH_2)_n$— and
(b) —$(CH_2)_m$—A—$(CH_2)_p$— in which n, m and p, which are identical or different, are each an integer from 1 to 6, and A is O, S, PR, SiR$_2$ or NR, in which R is C$_1$-C$_4$-alkyl, C$_5$-C$_6$-cycloalkyl, C$_6$-C$_{10}$-aryl, benzyl or phenethyl.

More advantageously, said bridge Z will be selected from the group consisting of (a1) —CH$_2$—,
(a2) —CH$_2$CH$_2$—,
(b1) —CH$_2$—O—CH$_2$—,
(b2) —CH$_2$—S—CH$_2$—,
(b3) —CH$_2$—P(Ph)—CH$_2$—,
(b4) —CH$_2$—Si(Me)$_2$—CH$_2$—,
(b5) —CH$_2$—Si(Ph)$_2$—CH$_2$—,
(b6) —CH$_2$—Si(Bz)$_2$—CH$_2$—,
(b7) —CH$_2$—Si(Et)$_2$—CH$_2$— or
(b8) —CH$_2$CH$_2$—P(Ph)—CH$_2$CH$_2$—.

Among these last bridges Z, the ones which are most valuable according to the invention are those containing a silyl group, namely the bridges of structures (b4) to (b7).

When R$^3$ is an alkoxy group, it preferably contains 1 to 6 carbon atoms.

The general method of preparing a phosphinite-borane compound of formula I$_o$ comprises the reaction of a phosphinite material substituted by BH$_3$ (i.e. an organometallic compound containing phosphorus and derived from a phosphinite product) of the formula

(II$_A$)

in which

R$^1$ and R$^2$ are defined as indicated above, and

Z$^1$ is Z or a first fragment of said bridge Z, with a phosphinite compound substituted by BH$_3$ of the formula

(III$_A$)

in which

R$^1$ and R$^3$ are defined as indicated above, and

Z$^2$ is R$^2$ or the second remaining fragment of the bridge Z, Z$^1$ and Z$^2$ being such that Z$^1$—Z$^2$=Z.

From a chiral point of view, the reaction of II$_A$ with III$_A$ can be illustrated by the following reaction mechanism:

Scheme 1

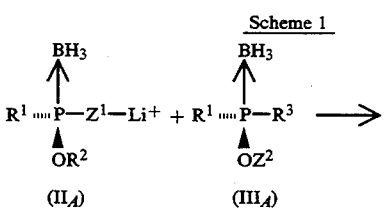

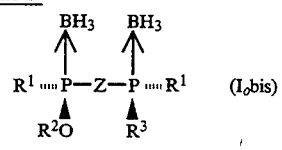

(I$_o$bis)

More precisely, the counterion of Li$^+$, namely X—, is a halide anion such as F—, Cl— or Br—, the preferred halide anion being Cl—.

In a first embodiment, structure (a1) given above, i.e. where Z=CH$_2$, is obtained by the reaction of one mol of II$_A$ (where Z$^1$ is CH$_2$) with at least one mol of III$_A$ (where OZ$^2$ is OMe).

This first embodiment is illustrated by the following reaction mechanism, in which Z$^1$ is CH$_2$, R$^1$ is Ph, R$^2$ is Me and R$^3$ is Me:

Scheme 2

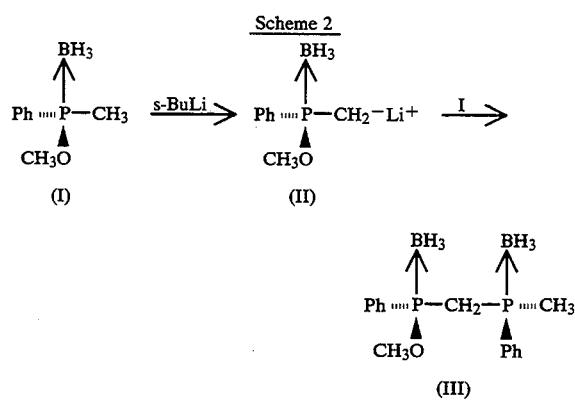

In a second embodiment, structure (a2) given above, i.e. where Z=CH$_2$CH$_2$, is obtained by the reaction of one mol of a compound II$_A$ (where Z$^1$ is CH$_2$) with one mol of the same compound II$_A$ (where Z$^1$ is also CH$_2$) in the presence of a mild oxidizing agent, preferably CuX$_2$ (where X is a halogen atom as defined above, advantageously Cl).

This second embodiment is illustrated by the following reaction mechanism, in which R$^1$ is Ph, R$^2$ is Me, R$^3$ is Me, Z$^1$ is CH$_2$ and Z is CH$_2$CH$_2$:

Scheme 3

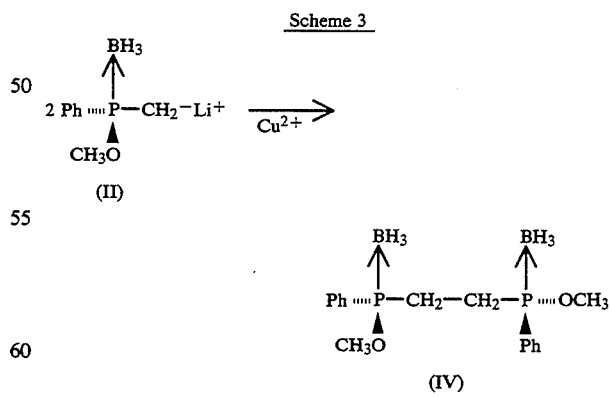

In a third embodiment, structures (b1-b7) given above can be obtained by the reaction of two mol of II$_A$ (where Z$^1$ is CH$_2$) with one mol of a dihalogenated compound of the formula

R$_2$AX$_2$ where R, A and X are defined as indicated above.

This third embodiment is illustrated by the following reaction mechanism, in which $R^1$ is Ph, $R^2$ is Me, $R^3$ is Me, $Z^1$ is $CH_2$ and Z is $CH_2$—$SiR_2$—$CH_2$ in the final product:

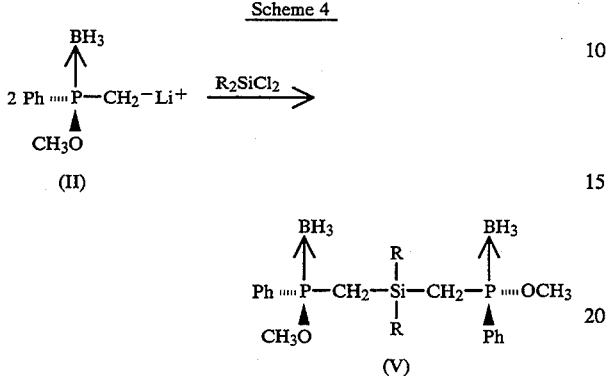

In the first, second and third embodiments, the reaction is carried out at a temperature of $-100°$ C. to $+30°$ C. In the first embodiment, a temperature gradient of $-40°$ C. to $+15°$ C. can be used. In the second embodiment, a temperature gradient of $-40°$ C. to $+20°$ C. can be used. In the third embodiment, a temperature gradient of $-40°$ C. to $0°$ C. can be used.

The preferred reaction solvent for carrying out the first, second and third embodiments is anhydrous THF.

The preferred temperature for carrying out the first, second and third embodiments is $0°$ C.

Furthermore, from a chiral point of view, an oxy group $OR^2$ or $R^3$ or both can be replaced in formula $I_o$ or $I_o$ bis with a group permitting nucleophilic substitution, i.e. a group which is more nucleophilic than said oxy groups $OR^2$ and $R^3$. For a replacement of this type, see the methods given especially in Examples 4 and 5 below.

BEST MODE

In the best mode of carrying out the invention, chiral compounds of formula $I_o$ (i.e., more precisely, of formula $I_o$ bis) are provided in which $R^1$ is Ph, Ph substituted by one to three alkoxy groups, where each alkoxy group contains from 1 to 4 carbon atoms, or 2-naphthyl, $R^2$ is a $C_1$-$C_6$-alkyl group, $R^3$ is a $C_1$-$C_6$-alkoxy group and Z is
—$CH_2$—$Si(Me)_2$—$CH_2$—,
—$CH_2$—$Si(Ph)_2$—$CH_2$—,
—$CH_2$—$Si(Bz)_2$—$CH_2$— or
—$CH_2$—$Si(Et)_2$—$CH_2$—.

These compounds are obtained in accordance with the reaction mechanism of scheme 4 given above.

Moreover, these compounds can be converted to other chiral products, namely, in particular,
(i) phosphinite-borane compounds of formula $I_o$ bis,
(ii) diphosphine-diborane compounds of formula X and
(iii) diphosphine compounds of formula IX, starting from said compounds of formula X.

The conversions (i) and especially (ii) referred to above are advantageously carried out according to a nucleophilic substitution mechanism, the oxy groups $OR^2$ and $R^3$ being replaced in particular with aryl groups, alkoxy-substituted aryl groups and alkyl groups.

In another embodiment of the invention, the diphosphine-diborane compounds can be synthesized directly in accordance with scheme 5 below, which relates to products having a bridge Z consisting of a heterohydrocarbon chain of the structure $CH_2$—A—$CH_2$ (where A is defined as indicated above and is advantageously $SIR_2$).

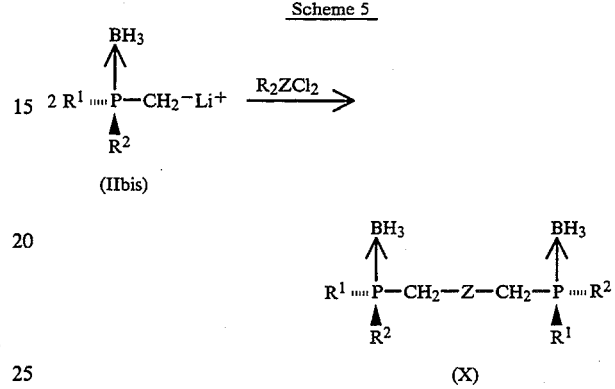

The compounds of formula X which are preferred according to the invention are those in which Z is a bridge
—$CH_2$—$Si(Me)_2$—$CH_2$—,
—$CH_2$—$Si(Ph)_2$—$CH_2$—,
—$CH_2$—$Si(Bz)_2$—$CH_2$— or
—$CH_2$—$Si(Et)_2$—$CH_2$—.

Other advantages and characteristics of the invention will be understood more clearly from the following description of Preparatory Examples. The technical data provided in said Preparatory Examples do not in any way imply a limitation but are given by way of illustration.

EXAMPLE 1

Methyl (1R,3R)-(—)-[methylphenylphosphino]methylphenyl-phosphinite-diborane

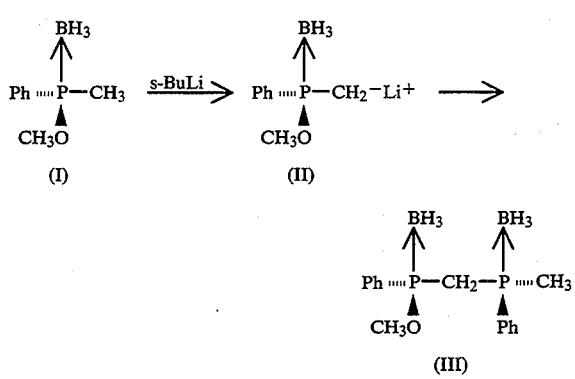

In a 50 ml round-bottomed flask, 2 mmol of phosphinite-borane I are dissolved in 3 ml of anhydrous THF at $-78°$ C. and under an inert atmosphere. 2 mmol of sec-butyllithium are added to this solution, with stirring. 0.25 h after this addition, the temperature of the reaction medium is brought slowly to $-40°$ C. and the temperature is kept at $-40°$ C. for 0.5 h to allow the anions II to form. After this time, a further 2 mmol of phosphinite-borane I are added, the temperature is raised slowly to +15° C. and the reaction medium is then left at this temperature for 2 h. After hydrolysis, evaporation of the solvent and washing with water, the expected product is extracted with $CH_2Cl_2$ and purified by filtration on silica using toluene as the eluent. Yield 70%

The characteristics of the product obtained are as follows: Colorless oil $[\alpha] = -56°$ (c=1; $CHCl_3$) $^1H$ NMR ($CDCl_3$): major signals: $\delta = 0.1$-1.5 (6H, qb, $^1J_{BH}=80$); 1.83 (3H, d, J=10.2); 2.60 (2H, m); 3.61 (3H, d, J=12.5); 7.25-7.5 (6H, m); 7.5-7.8 (4H, m) minor signals: $\delta = 1.56$ (3H, d, J=10.38); 3.35 (3H, d, J=11.8) $^{13}C$ NMR ($CDCl_3$): $\delta = 11.39$ (d, J=39); 30.19 (dd, J=23, J=32); 54.01 (s); 128.47-132.36 (aromatic) (minor signal: $\delta = 12.89$ (d, J=39)) $^{31}P$ NMR ($CDCl_3$): $\delta = +8.38$ (q, $^1J_{PB}=67.5$); +113.10 (q, $^1J_{PB}=69.8$) IR (pure): $\nu = 3057$; 2945 (C—H); 2385; 2254 (B—H); 1437; 1417; 1173; 1115; 1064; 1034

| Microanalysis for: $C_{15}H_{24}O_{11}B_2P_2$ | | |
|---|---|---|
| | calculated | found |
| molecular weight | 304.1332 | 304.1334 |
| % C | 59.21 | 58.01 |
| % H | 7.89 | 7.72 |

EXAMPLE 2

(S,S)-1,2-bis[Methoxyphenylphosphino]ethaneborane

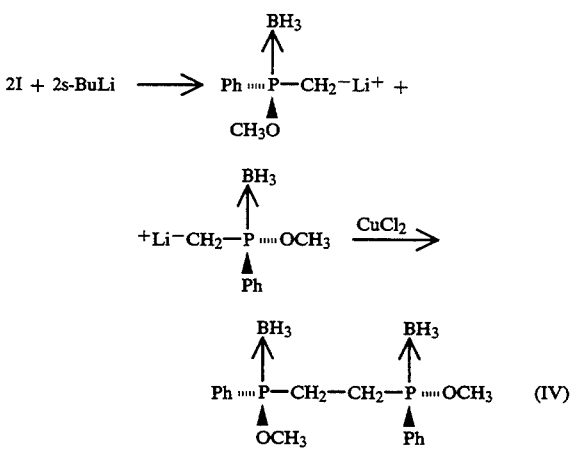

In a 50 ml round-bottomed flask, 2 mmol of phosphinite-borane I are dissolved in 3 ml of anhydrous THF at −78° C. and under an inert atmosphere. 2 mmol of sec-butyllithium are added to this solution, with stirring. 0.25 h after this addition, the temperature of the reaction medium is brought slowly to −40° C. and the temperature is kept at −40° C. for 0.5 h to allow the anions II to form. After this time, 10 mmol of $CuCl_2$ are added and the mixture is left to stand in air for 12 h. After hydrolysis, evaporation of the solvent and washing with water, the product is extracted with $CH_2Cl_2$ and purified by filtration on silica using toluene as the eluent. Yield 88%

M.p.=111°-115° C. $-^P$ $^{NMR}=+118$ ($J_{PB}=58$ Hz) $[\alpha]_D=-115.1°$ (c=1; $CHCl_3$) $^1H$ NMR=0-1.5 (6H, m); 1.9-2.4 (4H, m); 3.6 (6H, d); 7.4-7.8 (10, m) IR: $\nu_{BH}=2370$ cm$^{-1}$

EXAMPLE 3

(R,R)-bis[(Methoxyphenylphosphino)methyl]diphenylsilyl-borane

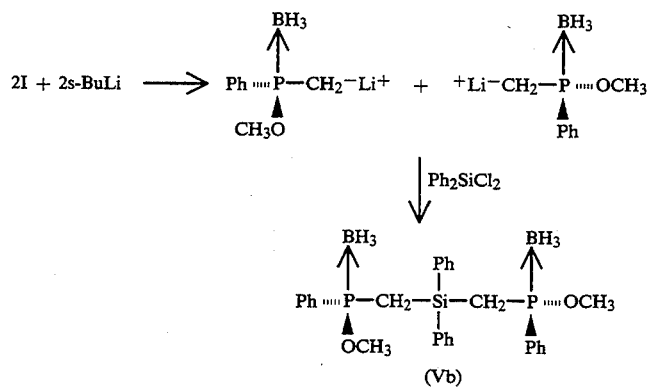

In a 50 ml round-bottomed flask, 2 mmol of phosphinite-borane I are dissolved in 3 ml of anhydrous THF at −78° C. and under an inert atmosphere. 2 mmol of s-butyllithium are added to this solution, with stirring. After 0.25 h, the temperature is brought slowly to −40° C. and left for 0.5 h at −40° C. to allow the anions II to form. After this time, 1 mmol of dichlorodiphenylsilane is added and the temperature is raised slowly to 0° C. and then kept for 2 h at 0° C. After hydrolysis, evaporation of the solvent and washing with water, the product is extracted with $CH_2Cl_2$ and purified by filtration on silica using toluene as the eluent. Yield 90%

Thick colorless oil $^1H$ NMR ($CDCl_3$): $\delta = 0.0$-1.5 (6H, qb, $^1J_{BH}=95$); 2.13-2.43 (4H, qd, J=7.7, J=16.4); 3.28 (6H, d, J=12.28); 7.05-7.85 (20H, m) (other diastereoisomer: 3.25 (6H, d, J=12.27)) $^{31}$P NMR ($CDCl_3$): $\delta = +116.74$ (m) (other isomer: $\delta = +114$ (m))

EXAMPLE 4

Use of the diphosphinite-borane IV of Example 2 in the preparation of DIPAMPborane VI

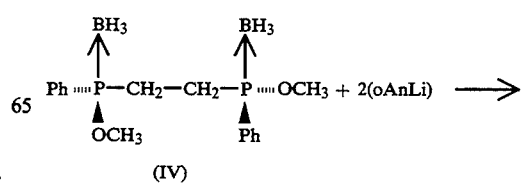

-continued

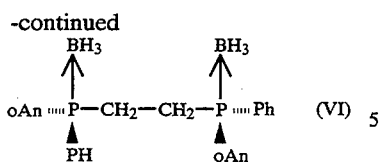

In a 50 ml round-bottomed flask, 2 mmol of phosphinite-borane IV are dissolved in 5 ml of anhydrous THF at −78° C. and under an inert atmosphere. 2.1 mmol of o-anisyllithium (oAnLi) are added to this solution, with stirring. 0.25 h after this addition, the temperature of the reaction medium is brought slowly to 0° C. over 2 h and the mixture is hydrolyzed. After evaporation of the solvent, washing with water and extraction with $CH_2Cl_2$, the product obtained is purified by filtration on silica using toluene as the eluent. Yield 80%

M.p.=163° C. (consistent with the literature)

EXAMPLE 5

Use of the diphosphinite-borane IV of Example 2 in the preparation of diphosphineboarane VIII

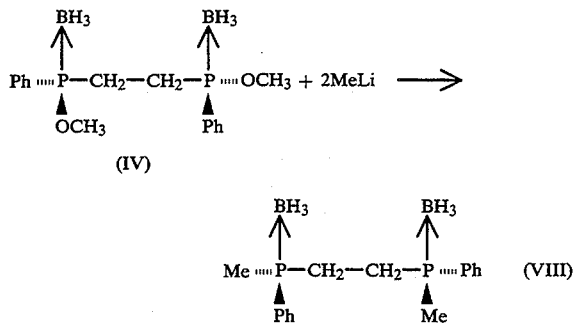

In a 50 ml round-bottomed flask, 2 mmol of diphosphinite-borane IV are dissolved in 5 ml of anhydrous THF at −78° C. and under an inert atmosphere. 2.1 mmol of methyllithium are added to this solution, with stirring. 0.25 h after this addition, the temperature of the reaction medium is brought slowly to 0° C. over 2 h and the mixture is hydrolyzed. After evaporation of the solvent, washing with water and extraction with $CH_2Cl_2$, the product obtained is purified by filtration on silica using toluene as the eluent. Yield 90%

M.p.=166°-168° C. IR: 2378, 1457, 1420, 1065 cm$^{-1}$ 1H NMR: 0-2 ppm (6H, m); 1.55 (6H, m); 1.8-2.2 (4H, m); 7.2-7.9 (1OH, m) Analysis for: $C_{16}H_{26}B_2P_2$ calculated: C=63.58% H=8.61% found: C=63.68% H=8.55%

EXAMPLE 6

Use of the diphosphine-boranes prepared in Examples 4 and 5 in the preparation of diphosphines According to the technique described in the prior art by T. Imamoto (this is the technique used in scheme 3, page 6358, of the article by S. JUGE et al. cited above), a 0.5M solution of (−)-DIPAMP-diborane VI is heated at 50° C. for 12 h. After this time, the excess amine is evaporated off and the residue is filtered on a short silica column using toluene as the eluent. The expected diphosphine, namely the product (−)-DIPAMP in the case in question, is recovered in the first fractions. M.p.=103° C. (consistent with the literature).

If the compound of formula VIII obtained according to Example 5 above is used as the starting material, the expected diphosphine, namely the compound of the formula

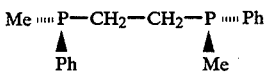

is obtained analogously.

EXAMPLE 7

(R,R)-bis[(o-Anisylphenylphosphino)methyl]diethylsilyl-diborane

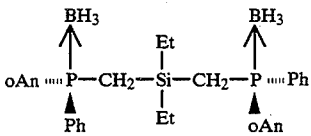

Scheme 5 is followed using a procedure similar to that described in Example 3 above.

2 mmol of diphosphine-diborane are dissolved in 3 ml of anhydrous THF at −70° C. and under an inert atmosphere. 2 mmol of s-BuLi are added to the resulting solution, with stirring. After the reaction medium has been stirred for 0.25 h, the temperature is brought slowly to −40° C. and kept at −40° C. for 0.5 h to allow the anions to form. After this time, 1 mmol of dichloroethylsilane is added and the temperature is raised slowly to 0° C. and kept for 2 h at 0° C. After hydrolysis, evaporation of the solvent and washing with water, the product is extracted with $CH_2Cl_2$ and purified by filtration on silica using toluene as the eluent. Recrystallization from ethanol gives the expected product in the form of white crystals. Yield 76%

M.p.=181° C. $[\alpha]_D=+86°$ C. $^1$H NMR (CDCl$_3$): 0-1.5 (16H, m); 1.7-2.4 (4H, m); 3.7 (6H, s); 6.8-8 (18H, m) $^{13}$C NMR (CDCl$_3$): 5.23; 6.7; 30.8; 55.1; 110.9; 120.7-135.9; 161 IR (KBr): 698; 747; 764; 781; 805; 1227; 1464; 1589; 2375

EXAMPLE 8

(R,R)-bis[(2,4-Dimethoxyphenylphenylphosphino)methyl]diphenylsilyl-diborane

The expected product is obtained with a yield of 92% by following the modalities described in Example 7 above.

M.p.=154° C. $[\alpha]_D=+61°$ $^1$H NMR (CDCl$_3$): 0-1.5 (6H, m); 2.6-2.9 (4H, m); 3.49 (6H); 3.78 (6H, s); 6.1-6.3 (2H, m); 6.9-7.7 (24H, m) $^{13}$C NMR (CDCl$_3$): 55.2 ($J_{pc}$=18 Hz); 98.4; 105; 126-135; 160-161

EXAMPLE 9

(R,R)-bis[(o-Anisylphenylphosphino)methyl]diphenylsilyl-diborane

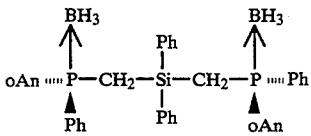

The expected product is obtained with a yield of 85%, after recrystallization from a hexane/toluene mixture (2/1 v/v), by following the modalities described in Example 7 above.

M.p.=200° C. $^1$H NMR (CDCl$_3$): 0–1.8 (6H, m); 2.85 (4H, d); 3.5 (6H, s); 6.5–7.5 (28H, m); 8 (d) $^{13}$C NMR (CDCl$_3$): 55; 110; 115–137 (m) IR (KBr): 689; 803; 1021; 1124; 1249; 1430; 1625; 2382

EXAMPLE 10

(S,S)-bis[(o-Anisylphenylphosphino)methyl]dimethylsilyl-diborane

If the starting material is o-anisylmethylphenylphosphine-borane [i.e. (S)-PAMP-BH$_3$], the expected product is obtained with an enantiomeric efficiency (abbreviated to e.e.) of 100%, after recrystallization from hexane, by following the modalities described in Example 7 above.

M.p.=139°–140° C. Rf (in toluene)=0.4 $^1$H NMR (CDCl$_3$): 0.2 (6H, s); 0.5–1.9 (6H, qb, $^1J_{BH}$=48.6); 1.8 (2H, t, J=13.5); 2.39 (2H, dd, J=13.8, J=18.2); 3.8 (6H, s); 6.95–8.18 (18H, m) $^{13}$C NMR (CDCl$_3$): 11.14 (d, J=27); 55.23 (s); 111.05 (s); 117.76–161.36 $^{31}$P NMR (CDCl$_3$): +12.4 (dm, J=56) IR (KBr): 1017; 1074; 1105; 1130; 1249; 1276; 1431; 1478; 1589; 2365 (B—H); 2403; 2972 (C—H); 3052

| Analysis for: C$_{30}$H$_{40}$O$_2$$^{11}$B$_2$P$_2$Si | | |
|---|---|---|
| | calculated | found |
| molecular weight | 544.2459 | 544.2435 |
| % C | 66.17 | 66-06 |
| % H | 7.35 | 7.42 |

EXAMPLE 11

(R,R)-bis[(2-Naphthylphenylphosphino)methyl]diphenylsilyl-diborane

If the starting materials are (S)-(methyl-2-naphthylphenylphosphine)-borane and dichlorodiphenylsilane, the expected product is obtained with an e.e. of 100%, after recrystallization from a hexane/propanol mixture (1/1 v/v), by following the modalities described in Example 7 above. M.p.=188° C. [α]$_D$=−2° (c=1; CHCl$_3$) $^1$H NMR (CDCl$_3$): 0.5–2.0 (6H, qb); 2.65 (4H, dt, J=14.2, J=76.6); 6.70–7.88 (32H, m); 7.97 (2H, d, J=13); 6.70–7.88 (32H, m); 7.97 (2H, d, J=13) $^{13}$C NMR (CDCl$_3$): 10.10 (d, J=24.2); 126.35–135.21 $^{31}$P NMR (CDCl$_3$): −12.6 (m)

EXAMPLE 12

(R,R)-bis[(Methoxyphenylphosphino)methyl]dimethylsilyl-diborane

The expected product is obtained with a yield of 93.7%, after recrystallization from toluene, by following the modalities described in Example 3 above.

M.p.=50° C. Rf=0.7 (in toluene) [α]$_D$=−89° C. (c=1; CHCl$_3$) $^1$H NMR (CDCl$_3$): 0.13 (6H, s); 0.4–1.8 (6H, qb, $^1J_{BH}$=100); 1.53 (4H, ddd, J=9.5, J=14.3, J=59.5); 3.52 (6H, d, J=11.9); 7.43–7.57 (6H, m); 7.71–7.82 (4H, m) [other diastereoisomer: 3.48 (6H, d, J=11.9)] $^{13}$C NMR (CDCl$_3$): 19.40 (d, J=33.5); 53.32 (s); 128.7 (d, J=9.6); 130.64 (d, J=11); 131.97 (s); 132.75 (s) $^{31}$ NMR (CDCl$_3$): major signal: +116.22 (q, $^1J_{BH}$=78) minor signal: +113.70 (q, $^1J_{BH}$=70) IR (pure): 1032; 1066; 1115; 1255 (C—O); 1437 (P—O); 2378 (B—H); 2841 (C—H); 2944; 3058

| Analysis for: C$_{18}$H$_{32}$O$_2$B$_2$P$_2$Si | | |
|---|---|---|
| | calculated | found |
| molecular weignt | 392.1832 | 392.1786 |
| % C | 55.10 | 55.60 |
| % H | 8.16 | 8.27 |

EXAMPLE 13

(R,R)-bis[(o-Anisylphenylphosphino)methyl]dimethyl-silyl-diborane

The expected product, which is the diastereoisomer of the product of Example 10, is obtained with a yield of 65%, after recrystallization from hexane, by following the modalities described in Example 7 above.

Example 14

(R,R)-bis[(o-Anisylphenylphosphino)methyl]diphenyl-silyl-diborane and
(S,S)-bis[(o-anisylphenylphosphino)methyl]diethylsilyl-diborane These two products are obtained from the diphosphinite-diborane of Example 3 and its diastereoisomer by removing the BH groups present on the phosphorus atoms in accordance with operating modalities analogous to those described in Example 4 above.

Starting from the product of Example 3, the product obtained is purified by filtration on silica using toluene as the eluent. After recrystallization from a hexane/toluene mixture (2/1 v/v), said pure product is obtained with a yield of 65%.

M.p.=200° C.

EXAMPLE 15

The diborane compound containing three phosphorus atoms of the formula

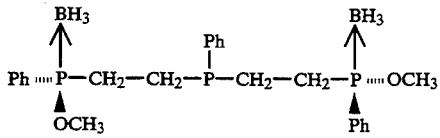

is obtained in accordance with scheme 4 by replacing R$_2$SiCl$_2$ with RP(CH$_2$Cl)$_2$.

The methoxy group is replaced with a group oAn by nucleophilic substitution to give the compound

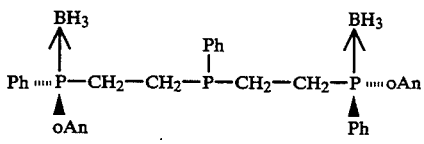

The triphosphine compound of the formula

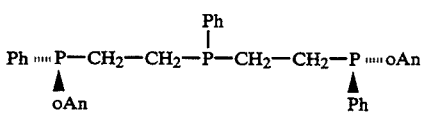

is obtained by removing the borane groups in accordance with the operating modalities of Example 6.

What is claimed is:

1. A chiral diphosphine-diborane compound of the formula

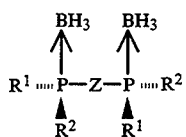 (X)

in which $R^1$ and $R^2$ which are identical or different each represent a $C_1$–$C_{18}$-alkyl, $C_5$–$C_{18}$-cycloalkyl, $C_7$–$C_{18}$-aralkyl or $C_6$–$C_{14}$-aryl group which may bear functional groups, and Z is $CH_2$—SiR—$CH_2$, where R is $C_1$–$C_4$-alkyl, $C_5$–$C_6$-cycloalkyl, $C_6$–$C_{10}$-aryl, benzyl or phenethyl.

2. A chiral diphosphine-diborane compound according to claim 1 which is selected from the group consisting of (R,R)-bis[(o-anisylphenylphosphino)methyl]diethylsilyldiborane, (S,S)-bis[(o-anisylphenylphosphino)methyl]diethylsilyldiborane, (R,R)-bis[(2,4-dimethoxyphenylphenylphosphino)methyl]diphenylsilyldiborane, (R,R)-bis[(o-anisylphenylphosphino)methyl]diphenylsilyldiborane, (S,S)-bis[(o-anisylphenylphosphino)methyl]dimethylsilyldiborane, (S,S)-bis[(2-naphtylphenylphosphino)methyl]diphenylsilyldiborane.

* * * * *